United States Patent

Hehrlein

[11] Patent Number: 5,947,889
[45] Date of Patent: Sep. 7, 1999

[54] BALLOON CATHETER USED TO PREVENT RE-STENOSIS AFTER ANGIOPLASTY AND PROCESS FOR PRODUCING A BALLOON CATHETER

[76] Inventor: Christoph Hehrlein, In der Aue 12, D-66118 Heidelberg, Germany

[21] Appl. No.: 08/875,236
[22] PCT Filed: Jan. 10, 1996
[86] PCT No.: PCT/DE96/00042
§ 371 Date: Jul. 18, 1997
§ 102(e) Date: Jul. 18, 1997
[87] PCT Pub. No.: WO96/22121
PCT Pub. Date: Jul. 25, 1996

[30] Foreign Application Priority Data
Jan. 17, 1995 [DE] Germany .................. 195 01 154

[51] Int. Cl.$^6$ .................................................. A61N 5/00
[52] U.S. Cl. ........................................ 600/3; 604/96
[58] Field of Search .................. 600/3, 6, 7; 604/96–102

[56] References Cited

U.S. PATENT DOCUMENTS

| | | | |
|---|---|---|---|
| 5,059,166 | 10/1991 | Fischell et al. | 600/3 |
| 5,302,168 | 4/1994 | Hess | 600/3 |
| 5,411,466 | 5/1995 | Hess | 600/203 |
| 5,499,980 | 3/1996 | Euteneuer | 606/28 |
| 5,782,742 | 7/1998 | Crocker et al. | 600/3 |

FOREIGN PATENT DOCUMENTS 0633041  1/1995  European Pat. Off. .

Primary Examiner—Linda C.M. Dvorak
Assistant Examiner—Rosiland Kearney
Attorney, Agent, or Firm—Paul Vincent

[57] ABSTRACT

A balloon catheter (1) is characterized by at least one radioactive nuclide species in or on the wall of the balloon (2) in order to eliminate vessel restrictions or stenoses and to inhibit restenosis in arteries (6), veins or vessel implants or to inhibit the growth of tumors, in which at least one radionuclide species is mixed with the plastic of the balloon wall, directly implanted into the balloon wall, or applied to the balloon wall as firmly adhesive film.

19 Claims, 3 Drawing Sheets

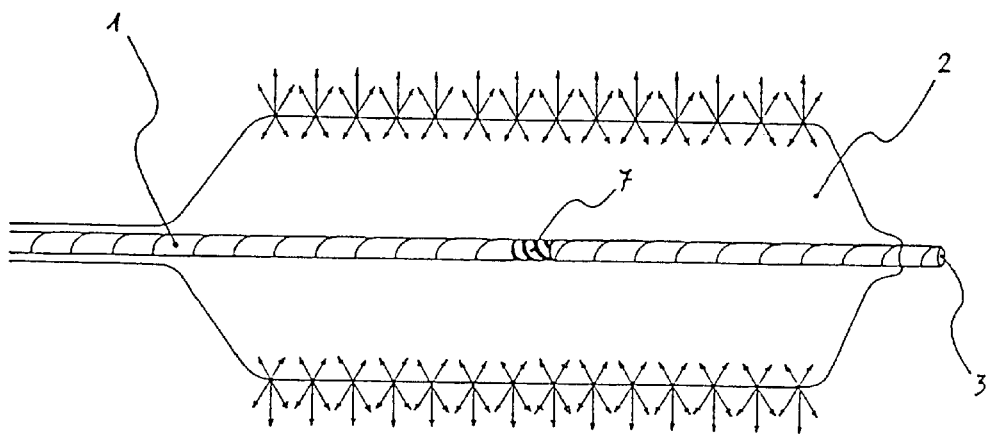
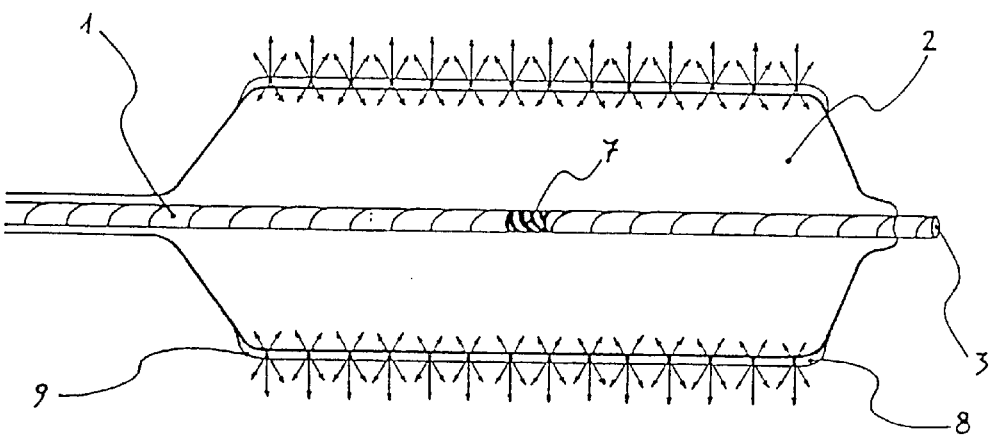

BALLOON CATHETER USED TO PREVENT RE-STENOSIS AFTER ANGIOPLASTY AND PROCESS FOR PRODUCING A BALLOON CATHETER

BACKGROUND OF THE INVENTION

The invention concerns a balloon catheter.

Angioplasty of a narrowing in a vessel or a vessel stenosis caused by arteriosclerosis using a balloon catheter leads to excessive multiplication of cells in the walls of the vessel in 30 to 50% of all treated patients which contributes to a restenosis of the vessel. The angioplasty triggers excessive cell production in the tissue of the cell wall as well as migration of smooth muscle cells of the tissue into the innermost layer of the artery. This process leads to so-called intimal hyperplasia which once more narrows the vessel.

There are other usable angioplasty methods for opening closed vessels via a laser or with atherectomy catheters for removing the stenostic material. These methods, as is the case with the balloon catheter, lead however to intimal hyperplasia.

The use of radioactive radiation to prevent excessive cell growth is known in the art for treatment of tumors or of intimal hyperplasia.

One possibility is to utilize radioactive radiation for the prevention of intimal hyperplasia through the temporary introduction of radioactive instruments or apparatus into the arteries or into a balloon catheter (U.S. Pat. No. 5,199,939 or U.S. Pat. No. 5,213,561). These methods have the disadvantage that the walls of the vessel are not evenly irradiated (U.S. Pat. No. 5,199,939) due to a poor centering of a thin radioactive wire or catheter or that there is no direct contact between the radioactive element and the walls of the vessel (U.S. Pat. No. 5,213,561 and EP 0 633 041 A1) so that large radiation doses are necessary to prevent the restenosis.

Pure beta-emitters are e.g. mainly effective at short ranges in the tissue and the effect of the radiation decreases significantly with increasing distance from the source location. High energy gamma-radiation emitted e.g. from the radioactive nuclide Iridium-192 (U.S. Pat. No. 5,213,561)) penetrates the radioactive element guiding catheter without large dose losses. However, the radiation dose is not completely absorbed in the walls of the artery, rather penetrates into the body of the patient. All catheters having radioactive elements must be sufficiently flexible and soft in consistency in order to avoid injuring the vessels.

One possibility of directly irradiating the walls of the vessel with low doses is the utilization of radioactive stents or vessel implants (EP patent 04 33 011 A1 and DE patent 43 15 002 C1). The implantation of stents can, however, lead to blood clots and to the sealing of the vessels due to the introduction of foreign materials into the human arteries which could result in destruction of tissue in the organ being treated. In addition, conventional clinically used stents can cause foreign allergic reactions resulting in the diffusion of infective cells into the walls of the vessel. In addition, for purposes of minimizing the radioactive dose on the entire organism, a rapid short-term radiative treatment is preferred rather than a long-term radiation treatment using a radioactive vessel implant.

The invention avoids the above-mentioned disadvantages. The invention concerns a balloon catheter, a method for its production and a partially manufactured product (balloon catheter having metallic coating) which can be transformed into a balloon catheter in accordance with the invention through radioactive transformation.

SUMMARY OF THE INVENTION

Radioactive elements should be localized on the surface of balloon catheter and be sufficiently plastically deformable to remain in direct contact with the walls of the vessel in the event of irregularities in the vessel walls (generally the case for arteriosclerosis in people). An important feature of the invention is the direct and even irradiation of the walls of the artery due to the flexibility of a balloon made from plastic combined with a homogeneous distribution of the radioactivity on or in the surface. This is guaranteed with the use of radioactive nuclides which are anchored in the walls of the balloon or introduced in a bonding fashion to the walls of the balloon in the form of a radioactive film. Radioactive nuclides are either directly implanted into the walls of the balloon or are produced through bombardment of a metallic film with charged particles.

A radioactive balloon can be utilized to simultaneously open up a narrowed vessel and, through the release of radiation into walls of the artery, prevent development of intimal hyperplasia and thereby a new stenosis. The additional introduction of a second apparatus or vessel implant to prevent intimal hyperplasia is then no longer necessary. It is preferred when the blood flow through the catheter is redirected during expansion of the balloon so that vessel closure time periods of up to one hour during expansion of the balloon can be tolerated by the patient. This is achieved using a so-called perfusion balloon catheter.

Radioactive nuclide species should be utilized in the wall of the balloon which preferentially have a short range (e.g. beta-emitters). Radioactive nuclides which substantially emit gamma-radiation are rather poorly suited in a radioactive balloon catheter to inhibit restenosis. The radiation is given-off in a sideward direction through the balloon as a result of which only the directly stretched walls of the vessel are irradiated. The activity on the ends of a balloon can be locally increased to prevent a decrease in the radiative dose at the ends of the balloon in the event of homogeneous activation of the balloon surface.

Further features and advantages of the invention can be derived from the following description of embodiments of the invention with regard to the drawing showing details which are important to the invention, as well as from the claims. The individual features can each be used in embodiments of the invention individually or collectively in arbitrary combination.

BRIEF DESCRIPTION OF THE DRAWING

FIG. 3 shows a longitudinal cut through an expanded balloon catheter with radioactive nuclides distributed in the wall of the balloon, FIG. 4 shows a longitudinal cut of an expanded balloon catheter having a polymer film comprising a radioactive nuclide species introduced onto its outer wall.

DESCRIPTION OF THE PREFERRED EMBODIMENT

Figure 1:
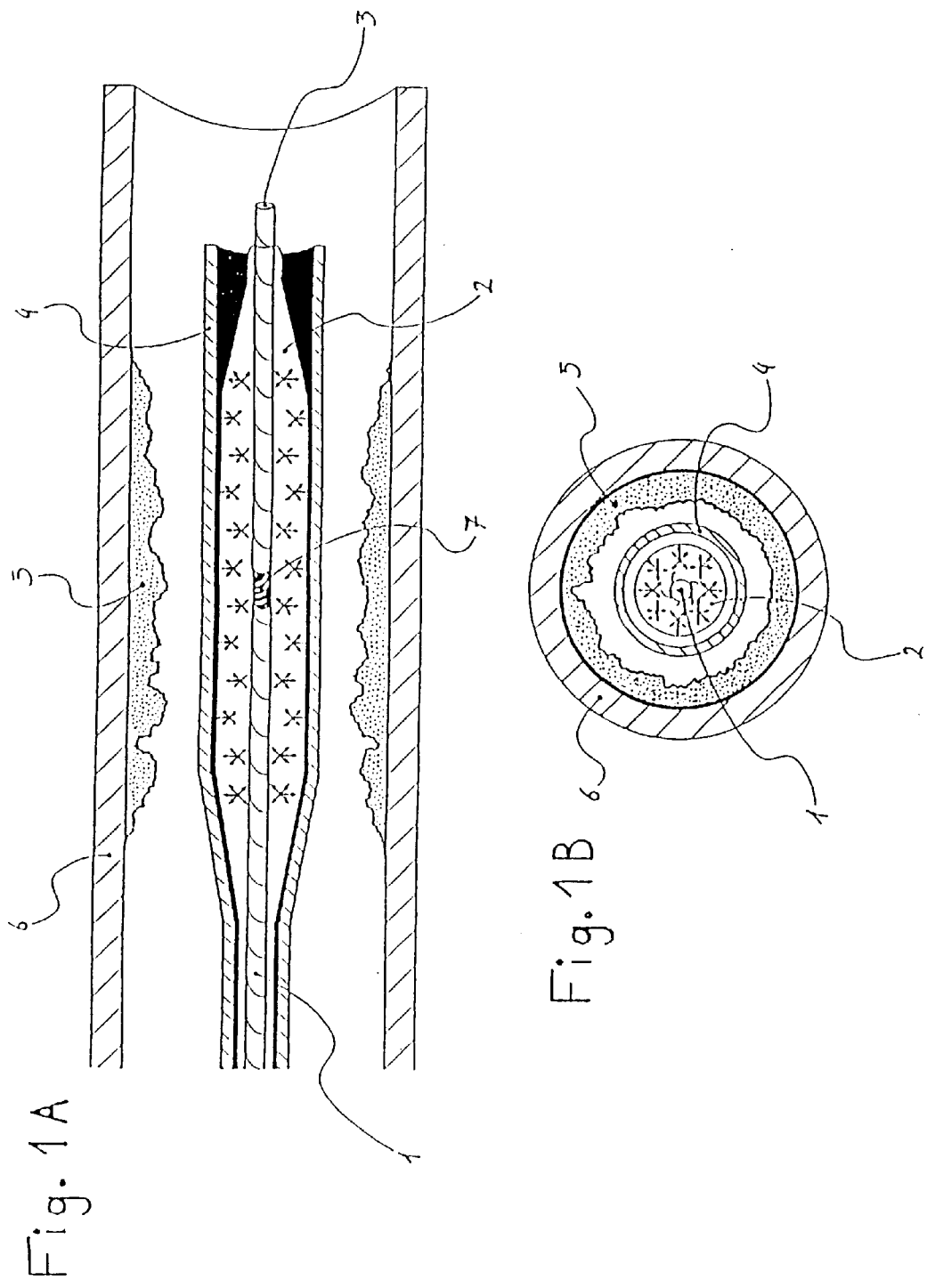
FIG. 1A shows a longitudinal cut through a balloon catheter within an artery and in the non-inflated state.
FIG. 1B shows a cross-section through FIG. 1A.
Figure 2:
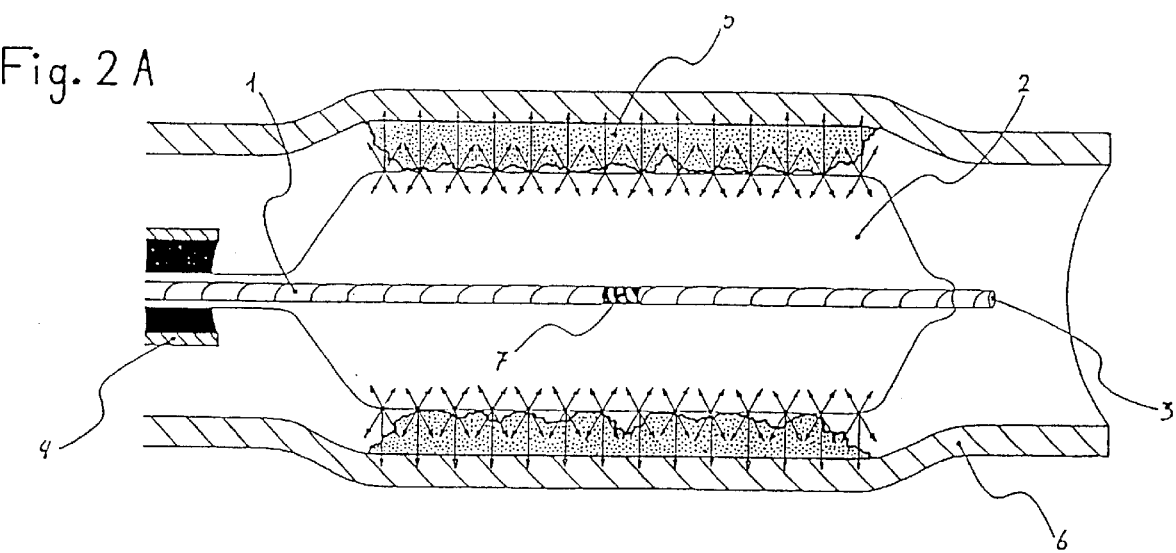
FIG. 2A shows a longitudinal cut through the balloon catheter in the artery and in the expanded state.
FIG. 2B shows a cross-section through FIG. 2A.
Figure 2:
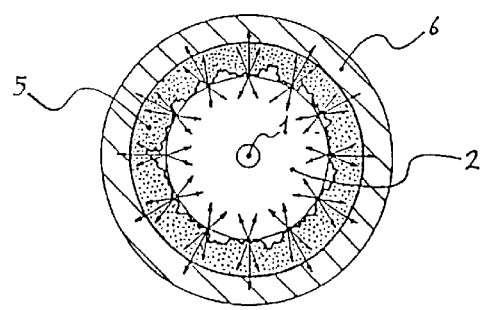

The balloon catheter in accordance with the invention comprises a catheter 1 having a folded radioactive balloon 2 at its tip (FIGS. 1A, 1B and 2A, 2B). A guiding wire can be pushed into the artery through the lumen 3 of the catheter. A flexible radiation-impermeable sheath 4 made from metal, e.g. made from lead or from a radiation-impermeable plastic, surrounds the balloon catheter (Tefzel™ Tube). The thickness of the sheath 4 assumes a value between 0.1 and 4 mm. This sheath is pulled back in the vicinity of the stenosis 5 at the location of treatment. It therefore serves to prevent radiation from being given-off during introduction and displacement of the balloon catheter, rather only at the location of treatment in the vicinity of the stenosis 5 in the artery 6. After the radiation protective sheath has been pulled back, the balloon can be inflated in the vessel. A marking 7 is located on the balloon catheter to indicate the middle of the balloon catheter.

In the expanded state (FIGS. 2A, 2B), the balloon is adjacent to the wall of the artery, enlarges the lumen of the vessel, and simultaneously emits radiation. Ionizing radiation is given-off by radioactive nuclides distributed directly in the wall of the balloon (FIG. 3). Alternatively, the balloon wall is coated with a film 8 made from metal or plastic containing the radioactive nuclide (FIG. 4). In addition, a radiation-permeable protective layer 9 can be present to prevent contamination of the surrounding tissue with radioactive material.

The range of the radiation in the tissue preferentially assumes values between 0.05–10 mm. The radionuclides, which emit Alpha-, Beta-, Gamma-radiation or soft X-rays are evenly distributed in the walls of the balloon. The half-life ($t_{1/2}$) of the radioactive nuclide species or the radioactive nuclide species mixture should assume values between 5 hours and 3 years so that storage of the balloon catheter is possible without large losses in activity. Possibilities for use as radioactive nuclide are e.g. Phosphorus-32 ($t_{1/2}$ 14.3 d) or Cobalt-55 ($t_{1/2}$ 17.8 h) which, by means of electron capture, converts into the nuclide species Iron 55 under the emission of soft X-ray radiation and having a life time of 2.7 years. These radioactive nuclides substantially work in short range in human tissue, i.e. the radiative dose beyond 10 mm is extremely low.

The activation of plastic material of the balloon catheter can be done using a variety of techniques.

The manufacture of a radioactive balloon can be effected by mixing at least one radioactive nuclide species into the plastic of the balloon, e.g. polyethylene or latex, prior to manufacture of the catheter (FIG. 3). The radioactive nuclide species are composite with the plastic wall. The radioactive balloon is then attached to the catheter using conventional processing technology. The balloon can be compressed and expanded without loss of radioactivity.

Alternatively, one can activate commercially available balloon catheters in an accelerator installation. All possible commercially available balloon catheters can be used which are approved for angioplasty. Towards this end, the wall of the balloon is expanded and irradiated with at least one radioactive nuclide. An ion source delivers the necessary radioactive nuclide species. The radioactive nuclide species is introduced into an accelerator installation and acts as a localized ion beam on the plastic. The matrix material of the plastic accepts the radioactive nuclide species. An even activation of the balloon surface can be achieved by rotating the balloon. In order e.g. to selectively implant the pure beta-radiator Phosphorus-32 into the balloon wall, same is previously separated from Phosphorus 31 using a mass separator in an accelerator facility. All commercially available balloon catheters can be activated, including perfusion catheters having a plurality of holes or lumina before and after the balloon to guarantee blood flow during expansion of the balloon.

Alternatively, a polymer film having at least one radioactive nuclide species 8 can be introduced in a bonding and permanent fashion onto the outer wall of a balloon catheter or a second, thinner plastic layer 9 is attached over the radioactive polymer film. This plastic layer is pervious to the radiation and prevents the separation of the film due to contact with blood and as well as separation of the film during expansion of the balloon (FIG. 4).

Exemplary methods for the production of a radioactive balloon catheter in accordance with the invention are described below.

EXAMPLE 1

The range of the radiation in the vessel coming from a radioactive balloon catheter should preferentially assume values of 0.05–10 mm. Radioactive nuclides emitting beta-radiation or soft X-ray radiation have a short range in the artery and are therefore best suited as components of the balloon wall or balloon layer. Activation of commercially available balloon catheters can be effected through direct implantation of radioactive nuclide into the wall of the balloon. The balloon is thereby bombarded with radioactive nuclide in an expanded state in an accelerator installation. An even activation of the surface of the balloon can be achieved by rotation of the balloon. The radioactive nuclide is accepted by the plastic material of the balloon wall. In order e.g. to selectively implant the pure beta-radiator Phosphorus-32 into the balloon wall, same can be previously separated from Phosphorus 31 utilizing a mass separator in an accelerator installation.

EXAMPLE 2

A metallic layer, preferentially made from aluminum, silver or stainless steel is evaporated onto the expanded balloon of a commercially available balloon catheter. The layer should assume values between 2 nm and 5 $\mu$m. Subsequent thereto, argon ions are bombarded for improved anchoring of the metallic layer to the plastic material. In addition, either a selected radioactive nuclide species is directly implanted into this metallic layer or the metallic layer is bombarded with charged particles such as protons. The particle bombardment leads to a conversion of the metallic ions into radioactive nuclides bound in the metallic layer.

I claim:

1. A medical device suitable for treatment of a blood vessel before, during and after an angioplasty procedure comprising;

catheter means having an inflatable balloon and adapted for insertion into the blood vessel; and radioactive emitter uniformly distributed, without gaps, along said inflatable balloon.

2. The device of claim 1, wherein said radioactive emitter is implanted into said balloon.

3. A medical device suitable for treatment of a blood vessel before, during and after an angioplasty procedure comprising:

catheter means having an inflatable balloon and adapted for insertion into the blood vessel; and a first coating disposed on a surface of said balloon, said first coating carrying a radioactive emitter, wherein said radioactive emitter is uniformly distributed, without gaps, along said inflatable balloon.

4. The device of claim 3, wherein said first coating comprises a metallic film, said metallic film being one of implanted with said radiation emitter and bombarded with charged particles.

5. The device of claim 4, wherein said metallic film comprises at least one of aluminum and silver.

6. The device of claim 3, wherein said first coating comprises a plastic film.

7. The device of claim 6, wherein said plastic film comprises a polymer.

8. The device of claim 3, wherein said first coating comprises polyethylene.

9. The device of claim 1, wherein said radioactive emitter is mixed into a plastic material of said balloon during manufacture thereof.

10. The device of claim 1, wherein said catheter means has openings before and after said balloon and further having a perfusion channel connected to said openings for administering medication.

11. The device of claim 1, wherein said catheter means has a lumen before and after said balloon for maintaining blood flow through the blood vessel when said balloon is inflated.

12. The device of claim 1, wherein said radioactive emitter emits at least one of $\alpha$-, $\beta$-, and low energy x-radiation.

13. The device of claim 12, wherein said emitter comprises phosphorus 32.

14. The device of claim 1, wherein said emitter emits radiation having a range between 0.05 to 10 mm in human tissue.

15. The device of claim 1, wherein said emitter has a radioactivity between 0.001 to 1000 mCi per cm of balloon length.

16. The device of claim 1, further comprising sheath means consisting essentially of radiation impermeable material disposed around said balloon in a collapsed state thereof, said sheath means adapted for removal from said balloon before treatment of the blood vessel.

17. The device of claim 1, wherein said balloon comprises polyethylene.

18. A medical device suitable for treatment of a blood vessel before, during and after an angioplasty procedure comprising:

catheter means having an inflatable balloon and adapted for insertion into the blood vessel;

radioactive emitter uniformly distributed, without gaps, along said inflatable balloon; and a coating disposed on an outside surface of said balloon and covering said radioactive emitter for reducing tissue contamination.

19. A medical device suitable for treatment of a blood vessel before, during and after an angioplasty procedure comprising:

catheter means having an inflatable balloon and adapted for insertion into the blood vessel;

a first coating disposed on a surface of said balloon, said first coating carrying a radioactive emitter, wherein said radioactive emitter is uniformly distributed without gaps along said inflatable balloon; and a second coating disposed on an outside surface of said balloon and covering said first coating for reducing tissue contamination.

\* \* \* \* \*